US007002018B2

(12) United States Patent
Kumar et al.

(10) Patent No.: US 7,002,018 B2
(45) Date of Patent: Feb. 21, 2006

(54) PROCESS FOR THE PREPARATION OF AMORPHOUS FORM OF TORSEMIDE

(75) Inventors: Yatendra Kumar, Haryana (IN); Om Dutt Tyagi, Haryana (IN); Nitin Maheshwari, Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 10/485,590

(22) PCT Filed: Aug. 2, 2002

(86) PCT No.: PCT/IB02/03013

§ 371 (c)(1),
(2), (4) Date: Jul. 30, 2004

(87) PCT Pub. No.: WO03/014086

PCT Pub. Date: Feb. 20, 2003

(65) Prior Publication Data

US 2004/0254223 A1    Dec. 16, 2004

(30) Foreign Application Priority Data

Aug. 3, 2001  (IN)  .............................. 830/DEL/01

(51) Int. Cl.
*C07D 211/72* (2006.01)

(52) U.S. Cl. ...................... 546/291; 546/293; 546/294; 546/346

(58) Field of Classification Search ................ 546/291, 546/294, 293, 346
See application file for complete search history.

(56) References Cited

U.S. PATENT DOCUMENTS

| RE30,633 | E  | 6/1981  | Delarge et al. ............. 424/263 |
| 4,743,693 | A  | 5/1988  | Topfmeier et al. .......... 546/291 |
| 4,822,807 | A  | 4/1989  | Topfmeier et al. .......... 514/347 |
| RE34,580 | E  | 4/1994  | Topfmeier et al. .......... 546/291 |
| 5,914,336 | A  | 6/1999  | Dreckmann-Behrendt .. 514/347 |
| 6,166,045 | A  | 12/2000 | Dreckmann-Behrendt et al. ........................... 514/347 |
| 6,399,637 | B1 | 6/2002  | Filić et al. .................. 514/347 |

FOREIGN PATENT DOCUMENTS

| WO | WO 00/20395     | 4/2000  |
| WO | WO 01/10441     | 2/2001  |
| WO | WO 01/70694     | 9/2001  |
| WO | WO 01/70694 A1 * | 9/2001 |
| WO | WO 01/87841     | 11/2001 |

OTHER PUBLICATIONS

Dupont et al., "Structure d'une Seconde Variété de la Torasémide", *Acta. Cryst.*, B34:2659-2662 (1978).

Dupont et al., "Structure Cristalline et Moléculaire d'un Diurétique de l'Alkyl-1 [(Phénylamino-4 pyridyl-3) sulfonyl]-3 Urée:la Torasémide ($C_{15}H_{20}N_4SO_3$)", *Acta. Cryst.*, B34:1304-1310 (1978).

* cited by examiner

*Primary Examiner*—Johann Richter
*Assistant Examiner*—Chukwuma Nwaonicha
(74) *Attorney, Agent, or Firm*—Jayadeep R. Desbmukh, Esq.

(57) ABSTRACT

The present invention relates to a simple and efficient process for the preparation of amorphous form of torsemide. The process includes recovering amorphous torsemide from a solution thereof in a suitable solvent comprising alcohols, ketones, chlorinated hydrocarbons, esters, nitriles, cyclic ethers, and mixtures thereof, by spray drying.

4 Claims, 1 Drawing Sheet

PROCESS FOR THE PREPARATION OF AMORPHOUS FORM OF TORSEMIDE

FIELD OF THE INVENTION

Figure 1:
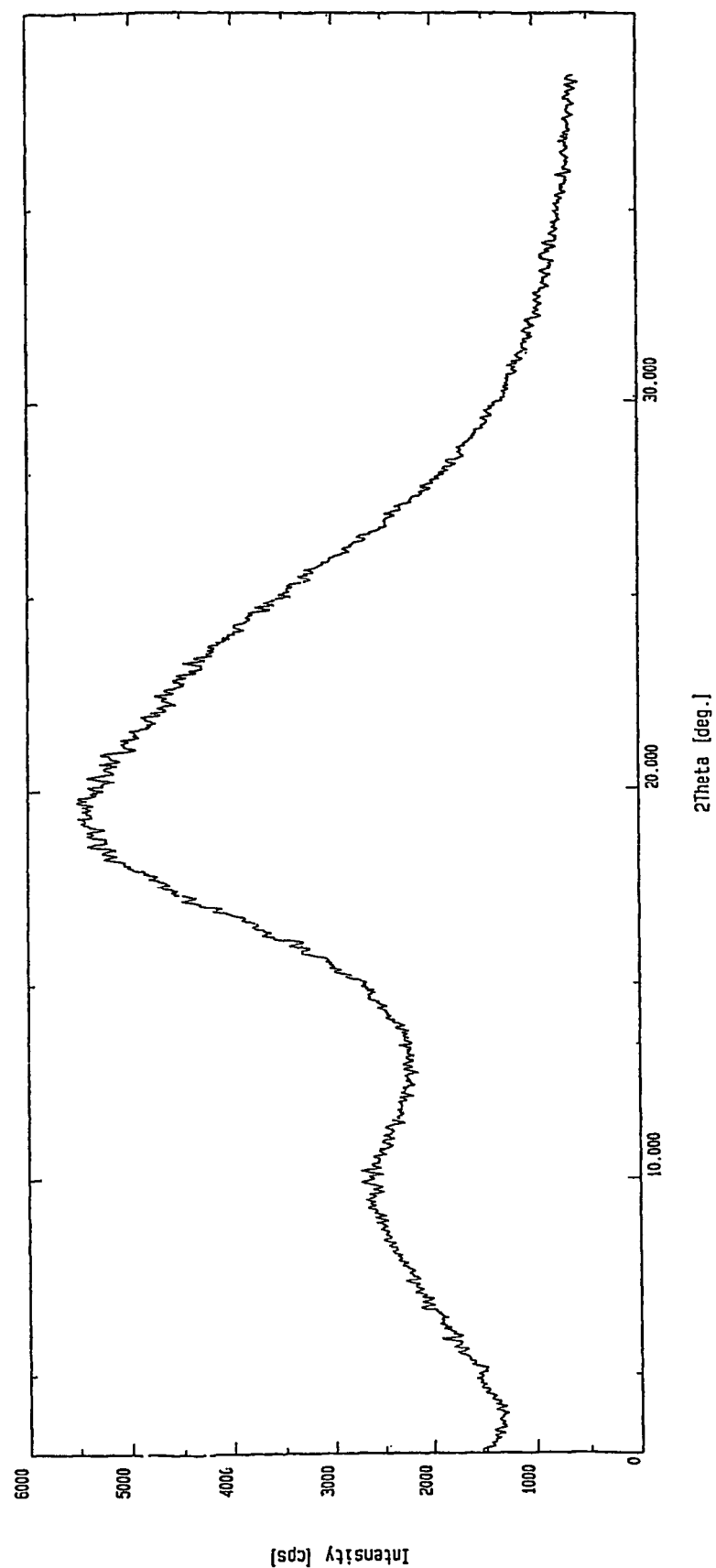

The present invention relates to a simple and efficient process for the preparation of amorphous form of torsemide.

BACKGROUND OF THE INVENTION

Chemically, torsemide is 1-isopropyl-3-[(4-m-toludino-3-pyridyl)-sulphonyl]-urea and has the structural formula I.

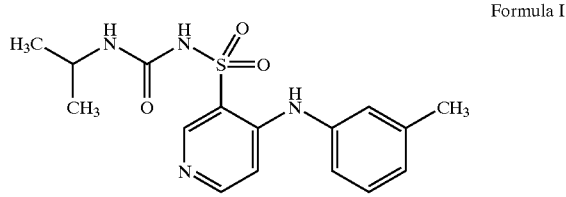

Formula I

Torsemide is used for the treatment of hypertension and edema associated with congestive heart failure, renal disease or hepatic disease. Torsemide is a loop diuretic whose primary site of action is the ascending limb of the loop of Henle. It has a sustained duration of action unlike standard loop diuretics. It is also used in the treatment of hypertension.

Torsemide has been reported to exist in different polymorphic forms. It is known that different morphs of biologically active compounds may have different absorption profile in vivo and consequently different pharmacokinetic profile. An amorphous form of torsemide has recently been disclosed in the PCT application, WO 01/10441. The process involves dissolving torsemide in water using ammonia gas or ammonium hydroxide, cooling the solution and isolating the amorphous torsemide by lyophilization or freeze drying. The process is unsuitable for industrial use as it involves cooling to low temperatures in the range of −50° to −80° C. and use of expensive techniques such as lyophilization or freeze drying. The process also involves the use of potentially hazardous ammonia gas and has the disadvantage of taking up to 80 hours thus rendering it uneconomical.

SUMMARY OF THE INVENTION

It is an objective of the present invention to provide an efficient method for the preparation of amorphous form of torsemide. The process does not involve drastic conditions of temperature or prolonged operations and is thus convenient to operate on a commercial scale and is operationally safe.

Accordingly, the present invention provides a process for the preparation of amorphous form of torsemide which comprises recovering amorphous torsemide from a solution thereof in a suitable solvent by spray drying.

The solution of torsemide may be obtained by dissolving crystalline torsemide in a suitable solvent or alternatively such a solution may be obtained directly from a reaction mixture in which torsemide is formed in a suitable solvent. The term "suitable solvent" includes alcohols, ketones, chlorinated hydrocarbons, esters, nitrites, cyclic ethers, and mixture(s) thereof. Examples of alcohol include methanol, ethanol, isopropanol, and the like. Examples of ketone include acetone, methyl isobutyl ketone and the like. Examples of chlorinated hydrocarbons include dichloromethane, dichloroethane, and the like. Examples of ester include methyl acetate, ethyl acetate, butyl acetate and the like. Example of nitrile include acetonitrile, and the like. Examples of cyclic ethers include tetrahydrofuran, dioxane, and the like.

The crystalline torsemide used as a starting material may be any of the various polymorphic forms known in the prior art such as modification I, modification II, modification III, form V, dupont form I, dupont form II etc. as disclosed in patents/patent applications/publications: U.S. Re30,633, U.S. Re34,580, U.S. Pat. No. 6,166,045, WO 00/20395, WO 01/10441, Acta Cryst., 2659 (1975) and Acta Cryst., 1304 (1978).

The spray drying may be accomplished using a spray dryer which operates on the principle of nozzle spraying in a parallel flow, i.e. the sprayed product and the drying gas flow in the same direction. The drying gas can be air or inert gases such as nitrogen, argon or carbon dioxide. Nitrogen is preferred in this case.

The amorphous torsemide prepared according to the process of the present invention was characterized by its X-ray powder diffraction, as shown in FIG. 1, pattern which gave a plain halo and showed no peaks, thus demonstrating the amorphous nature of the product.

DETAILED DESCRIPTION OF THE INVENTION

The present invention is further illustrated by the following example, which is not intended to limit the scope of this invention in any way.

EXAMPLE

Preparation of Amorphous Form of Torsemide

Crystalline torsemide (3.0 g) was dissolved in acetone (540 ml) at 45–50° C. The clear solution thus obtained was subjected to spray drying in a Mini Spray Dryer (Model Buchi—190) with an inlet temperature of 75–77° C. and an outlet temperature of 52–58° C. The fine powder of torsemide in an amorphous form was collected. It was further dried under vacuum at 30–35° C. to yield 1.8 g of torsemide of amorphous form. X-ray powder diffraction pattern showed a plain halo which demonstrates the amorphous nature of the product (FIG. 1).

While the present invention has been described in terms of its specific embodiments, certain modifications and equivalents will be apparent to those skilled in the art and are intended to be included within the scope of the present invention.

The invention claimed is:

1. A process for the preparation of amorphous form of torsemide which comprises recovering amorphous torsemide from a solution thereof in a suitable solvent consisting of alcohols, ketones, chlorinated hydrocarbons, esters, nitriles, cyclic ethers, or mixtures thereof, by spray drying.

2. The process of claim 1 wherein the solution is obtained directly from a reaction mixture in which torsemide is formed in a suitable solvent.

3. The process of claim 1 wherein the solution is obtained by dissolving crystalline torsemide in a suitable solvent.

4. The process of claim 1 wherein the solvent is selected from the group consisting of methanol, ethanol, isopropanol, acetone, methyl isobutyl ketone, dichloromethane, dichloroethane, ethylacetate, methylacetate, butylacetate, acetonitrile, tetrahydrofuran, dioxane, and mixtures thereof.

* * * * *